(12) United States Patent
Govea

(10) Patent No.: US 9,604,048 B2
(45) Date of Patent: Mar. 28, 2017

(54) LEADS WITH ELECTRODES DISPOSED IN MESH MATERIAL AND METHODS AND SYSTEMS USING THE LEADS

(71) Applicant: BOSTON SCIENTIFIC NEUROMODULATION CORPORATION, Valencia, CA (US)

(72) Inventor: Michael X. Govea, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/473,731

(22) Filed: Aug. 29, 2014

(65) Prior Publication Data

US 2015/0066122 A1    Mar. 5, 2015

Related U.S. Application Data

(60) Provisional application No. 61/874,285, filed on Sep. 5, 2013.

(51) Int. Cl.
*A61N 1/05* (2006.01)

(52) U.S. Cl.
CPC .............. *A61N 1/05* (2013.01); *A61N 1/0551* (2013.01); *A61N 1/0553* (2013.01); *Y10T 29/49117* (2015.01); *Y10T 29/49174* (2015.01)

(58) Field of Classification Search
CPC ....... A61N 1/05; A61N 1/0551; A61N 1/0553
See application file for complete search history.

(56) References Cited

U.S. PATENT DOCUMENTS

| | | | |
|---|---|---|---|
| 6,181,969 | B1 | 1/2001 | Gord |
| 6,397,109 | B1 | 5/2002 | Cammilli et al. |
| 6,516,227 | B1 | 2/2003 | Meadows et al. |
| 6,609,029 | B1 | 8/2003 | Mann et al. |
| 6,609,032 | B1 | 8/2003 | Woods et al. |
| 6,741,892 | B1 | 5/2004 | Meadows et al. |
| 7,244,150 | B1 | 7/2007 | Brase et al. |
| 7,437,193 | B2 | 10/2008 | Parramon et al. |
| 7,672,734 | B2 | 3/2010 | Anderson et al. |
| 7,761,165 | B1 | 7/2010 | He et al. |
| 7,949,395 | B2 | 5/2011 | Kuzma |
| 7,974,706 | B2 | 7/2011 | Moffitt et al. |
| 8,175,710 | B2 | 5/2012 | He |
| 8,224,450 | B2 | 7/2012 | Brase |

(Continued)

FOREIGN PATENT DOCUMENTS

WO    2009135075 A1    11/2009

OTHER PUBLICATIONS

International Search Report and Written Opinion for PCT/US2014/053566 mailed Nov. 5, 2014.

*Primary Examiner* — Tammie K Heller
(74) *Attorney, Agent, or Firm* — Lowe Graham Jones PLLC; Bruce E. Black

(57) ABSTRACT

An electrical stimulation lead has a distal end portion, a proximal end portion, and a longitudinal length and includes a lead body extending along the lead. The lead body includes an expandable mesh disposed along the distal end portion of the lead. The electrical stimulation lead also includes a number of electrodes attached to the mesh and a number of terminals disposed along the proximal end portion of the electrical stimulation lead. Further, the electrical stimulation lead includes multiple conductors electrically coupling the terminals to the electrodes.

10 Claims, 7 Drawing Sheets

(56) References Cited

U.S. PATENT DOCUMENTS

| | | |
|---|---|---|
| 8,364,278 B2 | 1/2013 | Pianca et al. |
| 2007/0150036 A1 | 6/2007 | Anderson |
| 2008/0009914 A1* | 1/2008 | Buysman et al. .............. 607/41 |
| 2009/0275996 A1* | 11/2009 | Burnes et al. .................... 607/2 |
| 2010/0100165 A1 | 4/2010 | Swanson et al. |
| 2011/0005069 A1 | 1/2011 | Pianca |
| 2012/0016378 A1 | 1/2012 | Pianca et al. |
| 2012/0046710 A1 | 2/2012 | DiGiore et al. |

\* cited by examiner

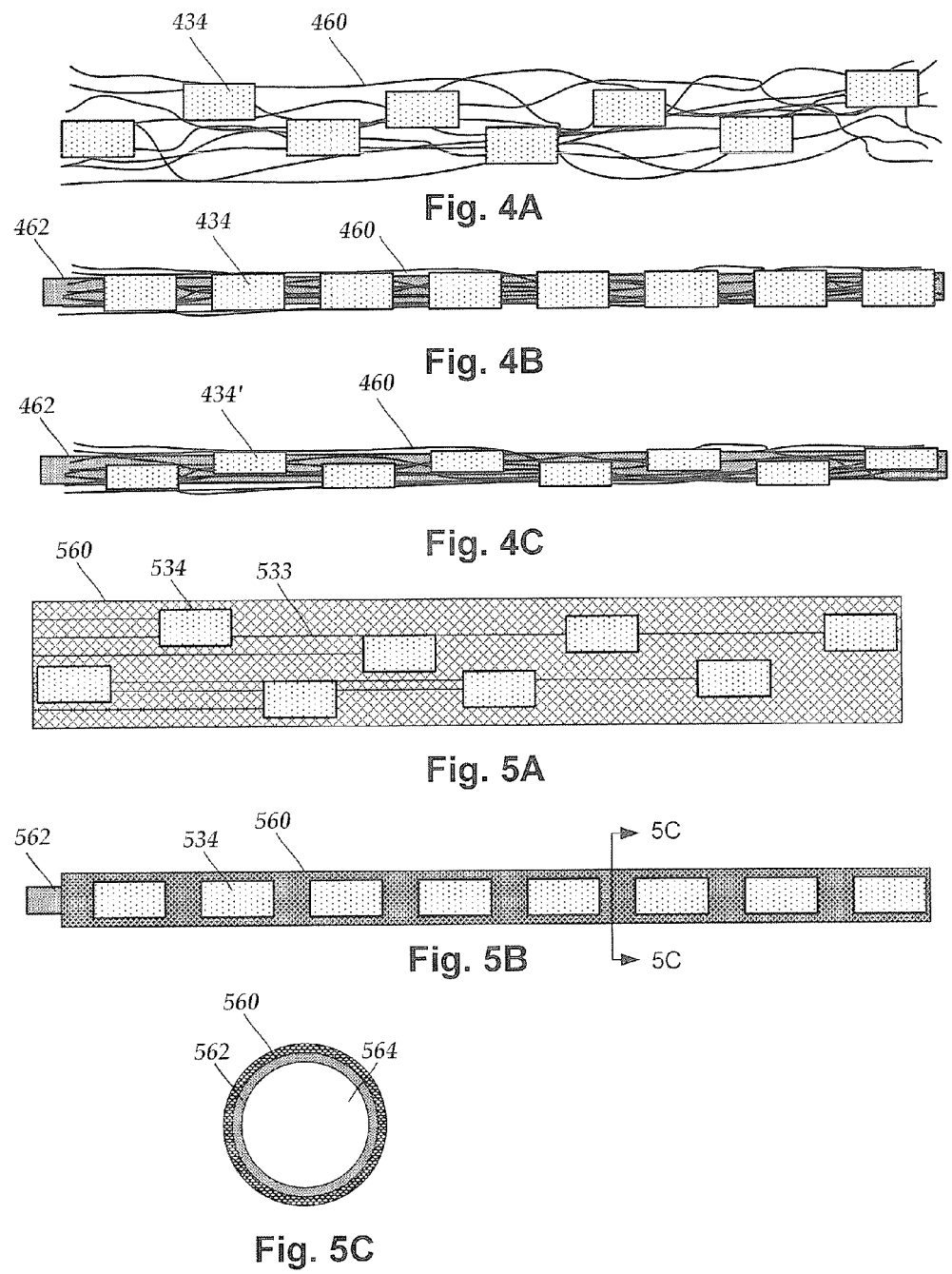

LEADS WITH ELECTRODES DISPOSED IN MESH MATERIAL AND METHODS AND SYSTEMS USING THE LEADS

FIELD

The present invention is directed to the area of implantable electrical stimulation systems and methods of making and using the systems. More particularly, the present invention is directed to implantable electrical stimulation leads having electrodes disposed in mesh material, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is an electrical stimulation lead with a distal end portion, a proximal end portion, and a longitudinal length. The electrical stimulation lead includes a lead body extending along the lead. The lead body includes an expandable mesh disposed along the distal end portion of the lead. The electrical stimulation lead also includes a number of electrodes attached to the mesh and a number of terminals disposed along the proximal end portion of the electrical stimulation lead. Further, the electrical stimulation lead includes a number of conductors that electrically couple the terminals to the electrodes.

Another embodiment is an electrical stimulation system including the electrical stimulation lead described above and a control module coupleable to the electrical stimulation lead. The control module includes a housing and an electronic subassembly disposed in the housing. The electrical stimulation system also includes a connector for receiving the electrical stimulation lead. The connector has a proximal end, a distal end, and a longitudinal length. The connector includes a connector housing defining a port at the distal end of the connector. The port can receive the proximal end of the lead body of the electrical stimulation lead. The connector further includes a number of connector contacts disposed in the connector housing. The connector contacts can couple to at least one of the terminals disposed on the proximal end of the lead body of the electrical stimulation lead.

Yet another embodiment is a method of making an electrical stimulation lead. The method includes attaching a number of electrodes to a mesh when the mesh is in an expanded state and then contracting the mesh to form, at least in part, a portion of the lead body with the electrodes in a desired electrode arrangement.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4A is a schematic side view of one embodiment of an expanded mesh and electrodes, according to the invention;

FIG. 4B is a schematic side view of the mesh and electrodes of FIG. 4A where the mesh has been contracted around a cylindrical element, according to the invention;

FIG. 4C is a schematic side view of another embodiment of a mesh and electrodes, according to the invention;

FIG. 5A is a schematic side view of a third embodiment of an expanded mesh and electrodes, according to the invention;

FIG. 5B is a schematic side view of the mesh and electrodes of FIG. 5A where the mesh has been contracted around a cylindrical element, according to the invention;

FIG. 5C is a schematic cross-sectional view of the arrangement of FIG. 5B, according to the invention;

DETAILED DESCRIPTION

The present invention is directed to the area of implantable electrical stimulation systems and methods of making and using the systems. The present invention is also directed implantable electrical stimulation leads having electrodes disposed in a mesh, as well as methods of making and using the leads and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
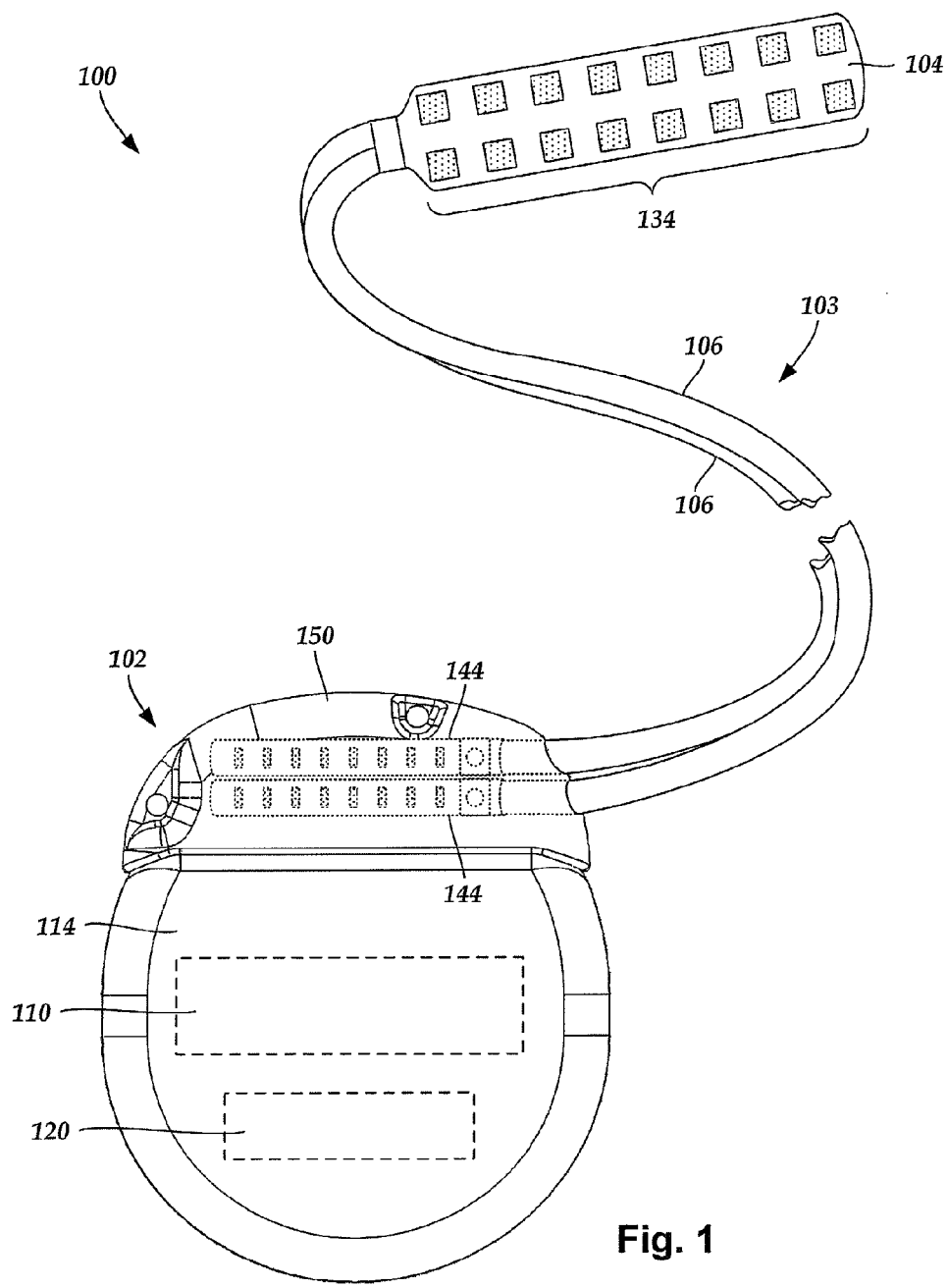
FIG. 1 is a schematic side view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133 (FIG. 2), such as electrode 134, is disposed on the paddle body 104, and an array of terminals (e.g., 310 in FIGS. 3A-3B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
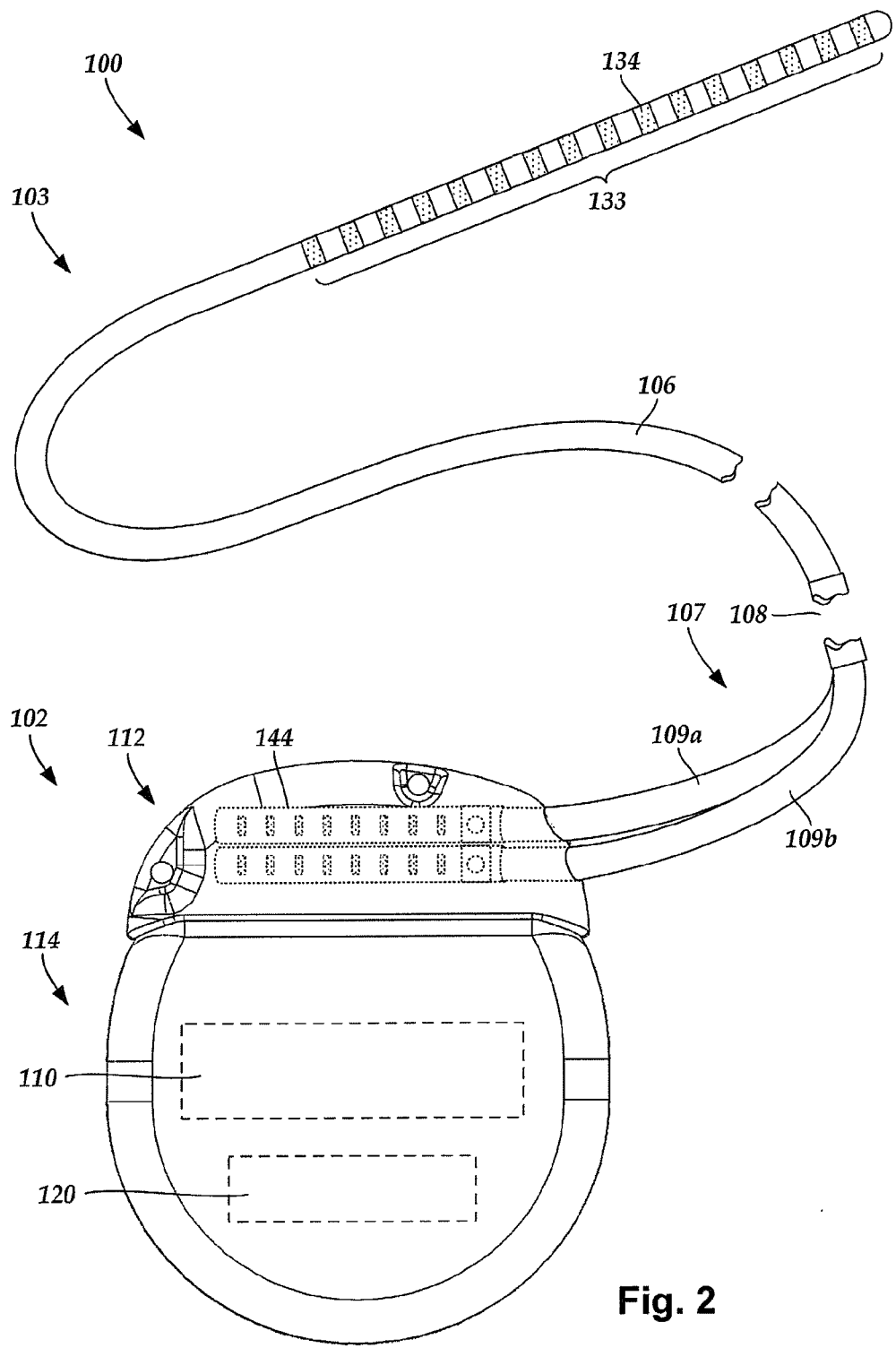
FIG. 2 is a schematic side view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (300 in FIGS. 3A-3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
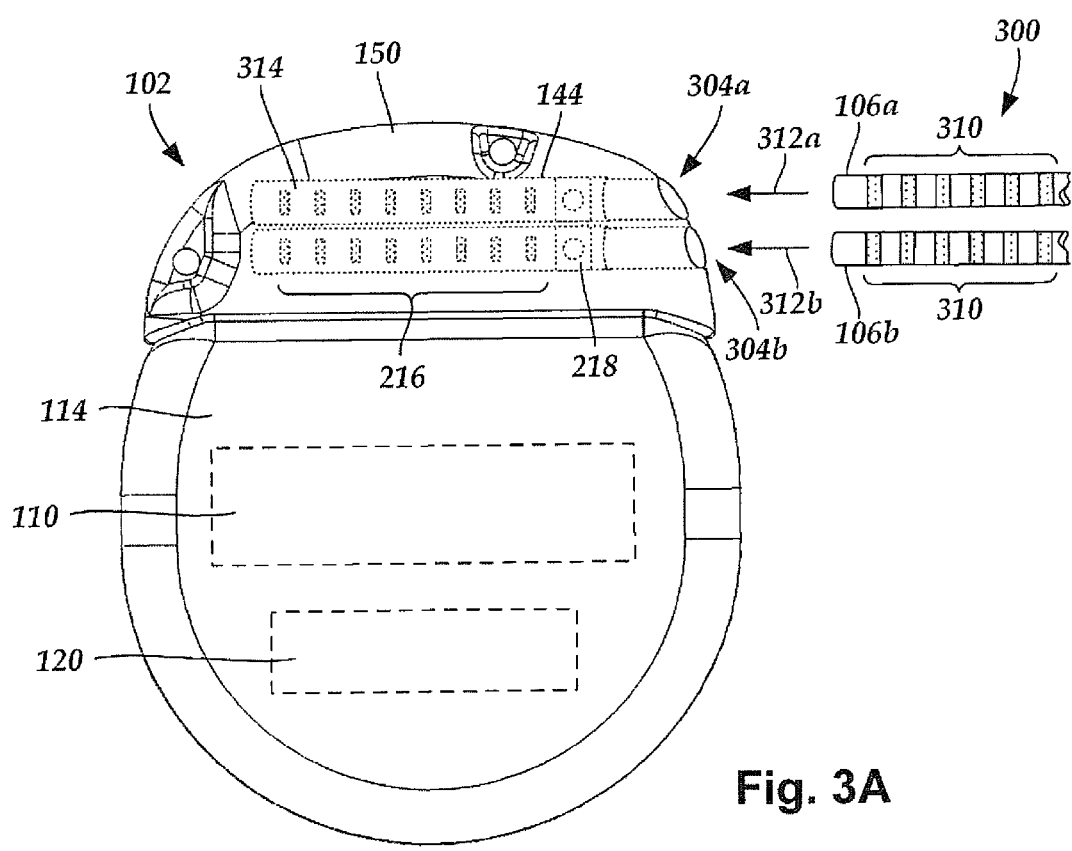
FIG. 3A is a schematic side view of one embodiment of the control module of FIG. 1 configured and arranged to electrically couple to an elongated device, according to the invention.
Figure 3B:
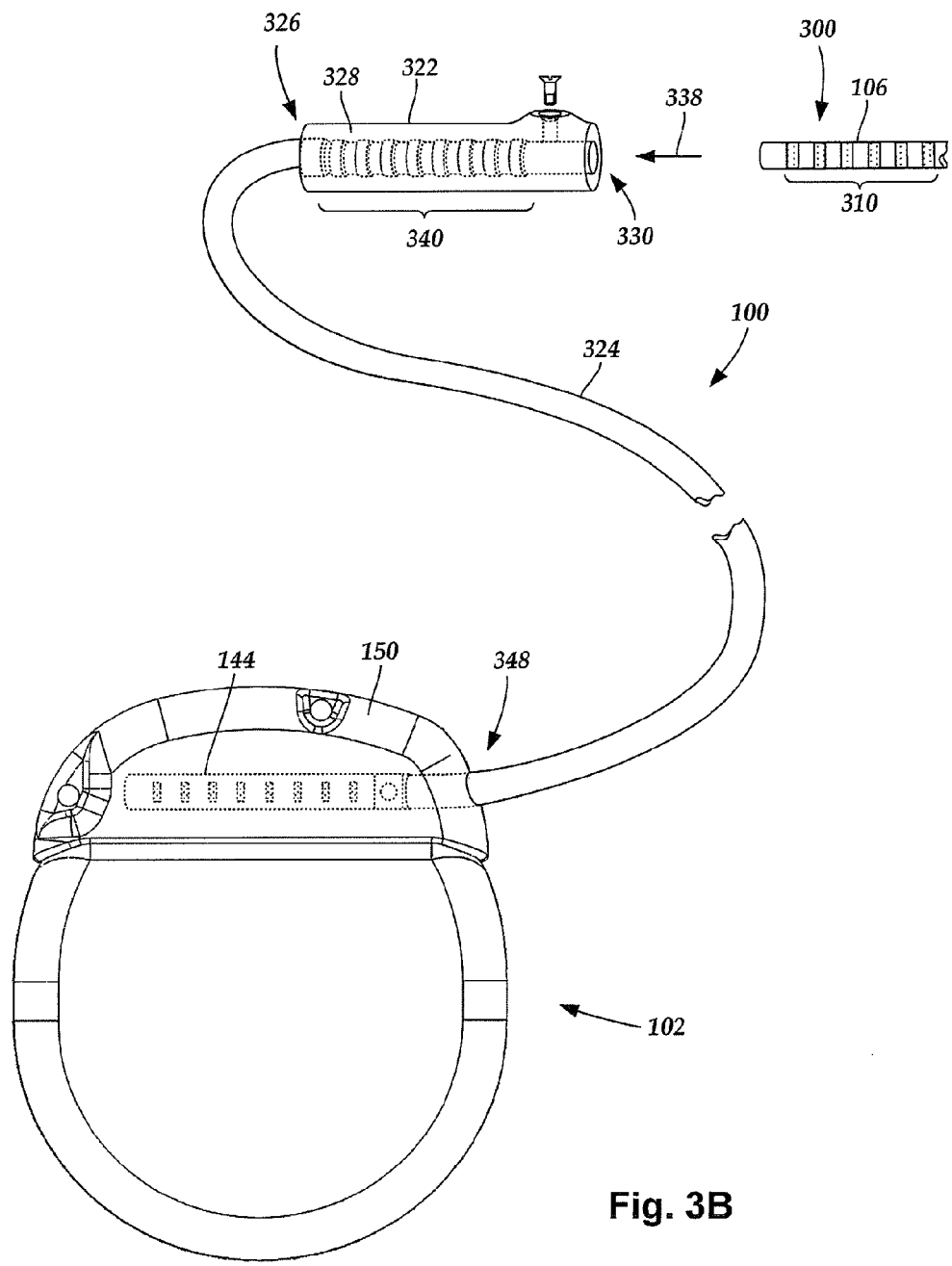
FIG. 3B is a schematic side view of one embodiment of a lead extension configured and arranged to electrically couple the elongated device of FIG. 2 to the control module of FIG. 1, according to the invention.

Terminals (e.g., 310 in FIG. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIGS. 3A-3B). The connector contacts are disposed in connectors (e.g., 144 in FIGS. 1-3B; and 322 in FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 107 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contacts 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

Leads, and the terminals and electrodes, attached to them are typically small in diameter and it may be challenging to correctly place the terminals or electrodes on the lead. This challenge may increase as the number of electrodes or terminals (or both) increase; particularly, as the number of electrodes or terminals is thirty-two or more. The positioning of electrodes or terminals (or both) can be facilitated by using an expandable mesh. The electrodes/terminals can be positioned on the mesh in its expanded state and the mesh can be contracted and coupled to the lead to give the desired electrode/terminal arrangement. Although the description below generally refers to electrodes, it will be understood that terminals or connector contacts can be positioned and placed on a lead or lead connector in the same manner.

FIG. 4A is a schematic side view of one embodiment of an expanded mesh 460 and a number of electrodes 434. The mesh 460 may include a number of strands, which are woven, knitted, entwined, interlocked or braided together. In at least some embodiments, the mesh forms a web-like structure. The mesh 460 can transit between an expanded state and a contracted state. The mesh 460 is expandable and can be expanded, for example, by reducing tension on the strands and contracted (or tightened such that the gap between the strands is reduced), for example, by applying tension on the strands. In at least some embodiments, the mesh 460 is contracted such that the mesh 460 contracts radially and stretches longitudinally. The mesh 460 can be a regular mesh with uniform arrangement of strands or an irregular mesh with non-uniform arrangement of strands. In some embodiments, the mesh 460 may be a combination of both the regular mesh and the irregular mesh.

As shown in FIG. 4A, the mesh 460 includes multiple strands loosely braided or otherwise entwined together in an expanded state. Examples of other types of mesh 460 may include plain mesh, twilled mesh, rectangular mesh, plain Dutch mesh, or any other suitable mesh. In some embodiments, the mesh 460 includes a number of lengthwise running strands and a number of crosswise running strands. In at least some embodiments, the lengthwise running strands are intertwined with the crosswise running strands such that the lengthwise running strands alternate between passing over or under the crosswise running strands. In at least some embodiments, such an arrangement may form a regular or a structured mesh with uniform gap between the strands.

In some embodiments, a twilled mesh may be used. The twilled mesh may be formed by weaving lengthwise running strands and crosswise running strands such that the lengthwise running strands alternate between passing over one and then under two or more crosswise running strands.

Further, in some embodiments, the mesh 460 can be a rectangular mesh or an oblong mesh, where lengthwise running strands and crosswise running strands of different diameters or dimensions are woven together and the gaps created by the may be rectangular or oblong. In alternative embodiments, a bundle of the lengthwise running strands may be woven together with a bundle of crosswise strands in any suitable arrangement.

In other embodiments, the mesh 460 may be a Plain Dutch mesh, in which the lengthwise running strands may be thicker than the crosswise running strands. The thicker crosswise running strands may be spaced apart from each other whereas the thinner lengthwise running strands may be disposed close to each other and may alternate between passing under and over the crosswise running strands.

The mesh 460 may be formed using suitable flexible or ductile biocompatible materials, particularly materials that form fibers. Such material may also be elastic or stretchable. Examples of suitable materials include PMMA (Poly (methyl methacrylate)), polyethylene, nylon, PEEK, terylene, and so forth. In at least some embodiments, the mesh 460 may be formed from Dacron™.

In at least some embodiments, the electrodes 434 are attached with the mesh 460 in an expanded state. The electrodes 434 may be attached to the mesh 460 using any suitable method, such as, but not limited to, intertwining, crimping, twisting, weaving, and so forth. The electrodes 434 may be ring electrodes, segmented electrodes or a combination of both. In some embodiments, the electrodes 434 are segmented electrodes. The segmented electrodes are grouped in sets, such that each set of the segmented electrode is disposed around the circumference of the lead at a particular longitudinal position. The segmented electrodes may be disposed at different locations with the lead body, such that, the location of the segmented electrodes may be in accordance with different coverage of target neurons. In at least some embodiments, the lead may include one, two, three or four sets of segmented electrodes. In some embodiments, the sets of segmented electrodes may be identically shaped, and sized. Examples of ring electrodes and segmented electrodes and arrangements containing these electrodes can be found at U.S. Patent Application Publications Nos. 2011/0005069, 2012/0016378, and 2012/0046710, all of which are incorporated herein.

In some embodiments, the electrodes 434 may be arranged within the mesh 460 in any suitable configuration such as along a helical pattern, a straight or curved line, staggered, circumferentially arranged in one or more rings, and so forth. The electrodes 434 may be formed using a suitable conducting biocompatible material, such as, but not limited to, stainless steel, titanium, platinum, gold, silver, any other suitable metal or alloy, and the like.

In at least some embodiments, the mesh 460 is formed by braiding strands of polymeric material. The mesh 460 is expanded or loosened by bringing the ends of the strands closer to each other until there are sufficient gaps created between the stands. Once the mesh 460 is expanded, the electrodes 434 are attached to or inserted within the mesh 460 by weaving the electrodes 434 into the mesh 460. Once the electrodes 434 are securely disposed within the gaps, the mesh 460 is contracted to form a portion of the lead body. For example, the mesh 460 can be contracted around a cylindrical element 462, such as a mandrel, single-lumen tube, or multi-lumen tube, to form a cylindrical lead body. An optional polymeric material or adhesive may be molded with the mesh 460 to fix the placement of the electrodes 434 and form a portion of the lead body.

FIG. 4B is a schematic side view of the mesh 460 and the electrodes 434 of FIG. 4A where the mesh 460 has been contracted around a cylindrical element 462. As shown, after the electrodes 434 are arranged on the mesh 460, the mesh 460 is contracted around the cylindrical element 462 by pulling the strands of the mesh 460 together, thereby reducing the gaps between the strands. The strands are pulled such that tension is applied longitudinally at the ends of the strands. In alternative embodiments, the mesh 460 may be cooled to contract the mesh 460 over the cylindrical element 462. Further, as shown in FIG. 4B, the electrodes 434 may become arranged in a desired electrode arrangement such as in a straight line, curved line, helix, or the like along a longitudinal length of the strands or the mesh 460 after the mesh 460 is tightened.

In some embodiments, contracting the mesh 460 includes contracting the mesh 460 around the cylindrical element 462 to form, at least in part, a portion of a cylindrical lead body. The cylindrical lead body may be part of a percutaneous lead with applications such as deep brain stimulation, spinal cord stimulation, and the like. The cylindrical element 462 may serve as a part of the lead body providing strength and stability to the lead body and prevent damage or deformation of the mesh 460. The cylindrical element 462 may be a hollow (e.g., single lumen) tube, multi-lumen tube, or a solid mandrel. The cylindrical element 462 can be formed using a suitable material such as, silicone, polyurethane, plastic, or the like.

The cylindrical element 462 may include a longitudinal lumen (See lumen 564 of FIG. 5C) defined to receive a stylet to facilitate implantation of lead. In some embodiments, the cylindrical element 462 may define one or more longitudinal lumens through which one or more conductors (for example, conductors 533 in FIG. 5A) may be passed. In some embodiments, each of the conductors may pass through a separate longitudinal lumen. However, in other embodiments, the conductors may pass through a single longitudinal lumen. In some embodiments, each electrode 434 may be attached to a separate conductor wire. Further, the cylindrical element 462 may include multiple openings (not shown) along the length of the cylindrical element 462, defined to receive the conductors. Further, a portion of each of the conductors may extend within one of the at least one longitudinal lumen of the cylindrical element 462. The conductors may electrically connect the electrodes 434 to the terminals (not shown) at the proximal end of the lead. In some embodiments, the conductors may extend through one or more openings within the longitudinal lumen of the cylindrical element 462 to connect the electrodes 434 to the terminals.

After attaching one or more electrodes 434 to the mesh 460 in an expanded state, the mesh 460 is contracted to obtain a desired electrode arrangement. In some embodiments, a polymeric material may be disposed over the mesh 460 to form a portion of a lead body. The polymeric material may be molded onto the mesh 460 to form the lead body. The polymeric material may be molded such that the polymeric material flows between the mesh 460 and the cylindrical element 462 and the polymeric material is not disposed over the top surface of the electrode 434. In at least some embodiments, the mesh 460 may include polymeric material coated over the mesh material. Heat may be then applied to allow the polymeric material to reflow thereby bonding the mesh 460 to the cylindrical element 462 to form the lead body.

In some embodiments, a bonding material such as, but not limited to, an adhesive, heat bonding material, pressure bonding material may be employed to form at least a portion of the lead body. Any biocompatible adhesive or bonding material can be used, including, but not limited to, epoxy resins, acrylic resins, polyurethane adhesives, colloidal epoxy silica, or the like. Any form of adhesive can be used, including, but not limited, to viscous, liquid, slurry, or the like.

As described above, a lead having large number of electrodes, such as thirty-two or more electrodes, can be formed with a desired electrode arrangement. Also, electrodes having small dimensions may be arranged in the desired electrode arrangement within the mesh in its expanded state. The mesh and the electrodes can be tightened to produce the desired final electrode arrangement.

FIG. 4C is a schematic side view of another embodiment of the mesh 460 and the electrodes 434'. As shown, the electrodes 434' are substantially small and are disposed regularly or irregularly with the mesh 460. In at least some embodiments, when the mesh is tightened the electrodes 434' may be substantially helically arranged with the mesh 460. Any other arrangement of electrodes 434' can be formed, such as zigzag, circular straight, staggered, or the like.

FIG. 5A is a schematic side view of a yet another embodiment of an expanded mesh 560 and a number of electrodes 534. As shown, the mesh 560 includes a number of strands arranged in a structured or regular manner in form of a net in an expanded form. In some embodiments, the strands of the mesh 560 do not extend lengthwise but, the net is formed from strands that are crisscross at an acute angle to the longitudinal axis of the mesh 560. The electrodes 534 may be disposed within the mesh 560 when the mesh 560 is in an expanded state such that a portion of the electrode 534 may be disposed within the gaps in the mesh 560. The electrodes 534 are coupled to one or more conductors 533 woven or otherwise entwined or disposed within the mesh 560. The conductors 533 electrically connect the electrodes 534 with terminals at a proximal end of a lead.

The lead may include a distal end portion, a proximal end portion and a longitudinal length. The lead may further include a lead body, the electrodes 534, and a number of terminals. The lead may also include a cylindrical element (cylindrical element 562 shown in FIG. 5A) disposed along at least the distal end portion of the lead. The mesh 560 may contract around the cylindrical element.

The lead also includes conductors 533 connecting the electrodes 534 with the terminals. The number of conductors 533 may vary in different embodiments. In some embodiments, each of the electrodes 534 may be coupled to a separate conductor wire, which would allow each electrode 534 to be controlled individually. To electrically isolate the conductors 533 running across the mesh 560, the conductors 533 may include an insulating coating disposed over the conductors 533.

The lead body includes the expandable mesh 560 disposed along the distal end of the lead. The lead body may also include a polymeric material, adhesive, or other bonding material intimately disposed with the mesh 560 to form a portion of the lead body.

FIG. 5B is a schematic side view of the mesh 560 and the electrodes 534 of FIG. 5A in a contracted state. After the electrodes 534 are secured within the mesh 560, the mesh 560 may be contracted around the cylindrical element 562 may be by pulling the strands of the mesh 560 longitudinally. After mesh 560 is contracted, the electrodes 534 are tightly secured with the mesh 560. The conductors 533 may pass through the cylindrical element 562 over which the mesh 560 is disposed.

FIG. 5C is a schematic cross-sectional view of the arrangement of FIG. 5B. As shown, the mesh 560 is disposed around the cylindrical element 562. The cylindrical element 562 defines the lumen 564 that may completely or partially extend longitudinally along a length of the cylindrical element 562. The conductors 533 may run through the lumen 564 of the cylindrical element 562. In some embodiments, the cylindrical element 562 defines more than one lumen 564 such that one lumen may receive the conductors 533 whereas, the other lumen may be defined to receive a stylet. In the illustrated embodiment, the mesh 560 is disposed around the cylindrical element 562 with a circular cross-section. However, any other cross-sectional shape of the cylindrical element 562 may be used. The cross-sectional shape of the lumen 564 may also vary.

Figure 6A:
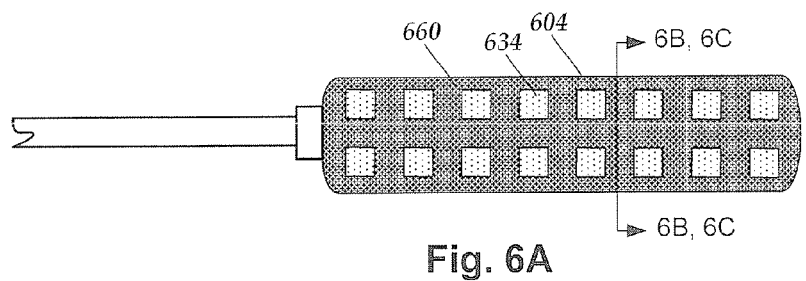
FIG. 6A is a schematic side view of one embodiment of a mesh and electrodes formed into a paddle body, according to the invention.

FIG. 6A is a schematic side view of one embodiment of a mesh 660 and a number of electrodes 634 formed into a paddle body 604. As shown, the mesh 660 or at least a portion of the mesh 660 is arranged in a form of a paddle at the distal end portion of the lead. Further, the mesh 660 includes the electrodes 634 arranged in an array as described with reference to FIG. 1. After arranging the electrodes 634 within the mesh 660, the mesh 660 may be contracted onto a substrate (such as paddle substrate 668 in FIGS. 6B and 6C) to form, at least in part, the paddle body 604. Thereafter, an optional polymeric material may be molded onto the mesh 660 to form, at least in part, the portion of the lead body i.e. the paddle body 604. Additionally or alternatively, an optional bonding material, such as an adhesive, may be applied onto the mesh 660 to form, at least in part, the portion of the lead body 604.

The paddle lead may have applications in spinal cord stimulation. As shown, the electrodes 634 are disposed in form of a 2×8 matrix. However, any other suitable electrode arrangements may be used such as, but not limited to, 2×4, 4×4, 4×8, or the like. The paddle body 604 may extend distally to the lead body such that conductors (such as conductors 533 shown in FIG. 5A) may travel within the lead body from the electrodes 634 to the terminals electrically coupling the electrodes 634 with the terminals.

Figure 6B:
FIG. 6B is a schematic cross-sectional view of one embodiment of the arrangement of FIG. 6A where the mesh surrounds a substrate, according to the invention.

FIG. 6B is a schematic cross-sectional view of one embodiment of the arrangement of FIG. 6A where the mesh 660 surrounds the paddle substrate 668. In the illustrated embodiment, the mesh 660 completely surrounds the paddle substrate 668. However, in other embodiments, the mesh 660 may partially surround the paddle substrate 668. The paddle substrate 668 may be an elongated body with an oblong cross-section. The paddle substrate 668 may include one or more lumens through which conductors may be routed to a proximal end of the paddle lead.

Figure 6C:
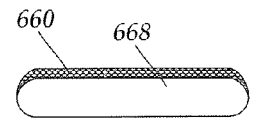
FIG. 6C is a schematic cross-sectional view of another embodiment of the arrangement of FIG. 6A where the mesh is disposed on a substrate, according to the invention.

FIG. 6C is a schematic cross-sectional view of another embodiment of the arrangement of FIG. 6A where the mesh 660 is disposed upon a top surface of the paddle substrate 668. In the illustrated embodiment, the mesh 660 is disposed upon the paddle substrate 668 along only a top surface of the paddle substrate 668. The mesh 660 may be attached to the paddle substrate 668 using a suitable method, such as, but not limited to, adhesive or physical bonding, heating, or the like.

Figures 7A, 7B, 7C:
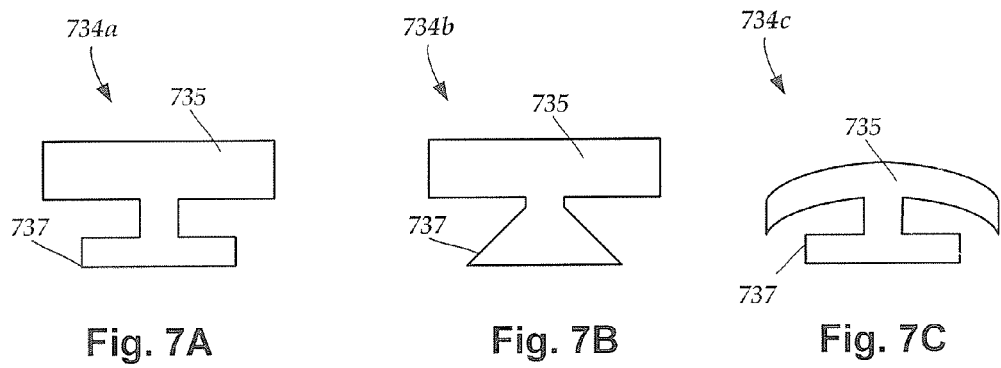
FIG. 7A is a schematic side view of one embodiment of an electrode for attachment to a mesh, according to the invention.
FIG. 7B is a schematic side view of another embodiment of an electrode for attachment to a mesh, according to the invention.
FIG. 7C is a schematic side view of a third embodiment of an electrode for attachment to a mesh, according to the invention.

FIG. 7A is a schematic side view of one embodiment of an electrode 734a for attachment to a mesh (such as, mesh 660 of FIG. 6A). The electrode 734a includes an electrode body 735 and a hook element 737 that may be fixedly attached to the mesh to hold the electrode 734a in place within the mesh. The electrode body 735 defines a substantially flat surface that may be designed to create good contact between the lead body to the tissue for conduction of electrical current. Electrodes such as electrode 734a and electrode 734b with a flat surface of contact may be suited for use in paddle leads.

The electrode body 735 may be joined to the hook element 737 through a linking member extending substantially orthogonal from the electrode body 735 to the hook element 737. The linking member may have a smaller cross-section so that it can be inserted into the gaps between the strands of the mesh. The hook element 737 may also define a substantially flat portion that is larger in dimensions than the linking member.

The hook element 737 may be designed to stay in place beneath the mesh after passing through the gaps between the strands of the mesh. Further, once the hook element 737 is secured beneath the mesh, the electrode body 735 remains disposed over the mesh.

To enhance the stability of the electrode 734 with the mesh, the hook element 737 may be woven, crimped, twisted, or otherwise coupled with one or more strands of the mesh. In some embodiments, the hook element 737 and the electrode body 735 may be separately formed and coupled together later. In some embodiments, the electrode may form an integral structure. The electrode 734a may be monolithically formed using a known technique such as molding, drawing, etching, grinding, stamping, machining, or the like.

FIG. 7B is a schematic side view of another embodiment of an electrode 734b for attachment to a mesh (for example, mesh 660 in FIG. 6A). The electrode 734b includes an electrode body 735, similar to the electrode body 735 disclosed in FIG. 7A. As shown, the electrode 734b includes a hook element 737 having a conical or a pyramidal shape. As shown in illustrated embodiment, the hook element 737 may be formed form an integrated piece with a tapered cross-section such that it is designed to be capable of insertion into the mesh and staying in place after insertion.

FIG. 7C is a schematic side view of a third embodiment of an electrode 734c for attachment to a mesh (for example, mesh 460 in FIG. 4A). In the illustrated embodiment, the electrode body 735 of the electrode 734c possesses an arcuate shape or a dome shape with a curved surface of contact. The electrode body 735 with the arcuate shape may be used with cylindrical leads, such as a percutaneous lead with a substantially circular cross-section. As shown, the hook element 737 defines a flat structure that can be secured within the mesh to attach the electrode 734c with the mesh.

Figure 8:
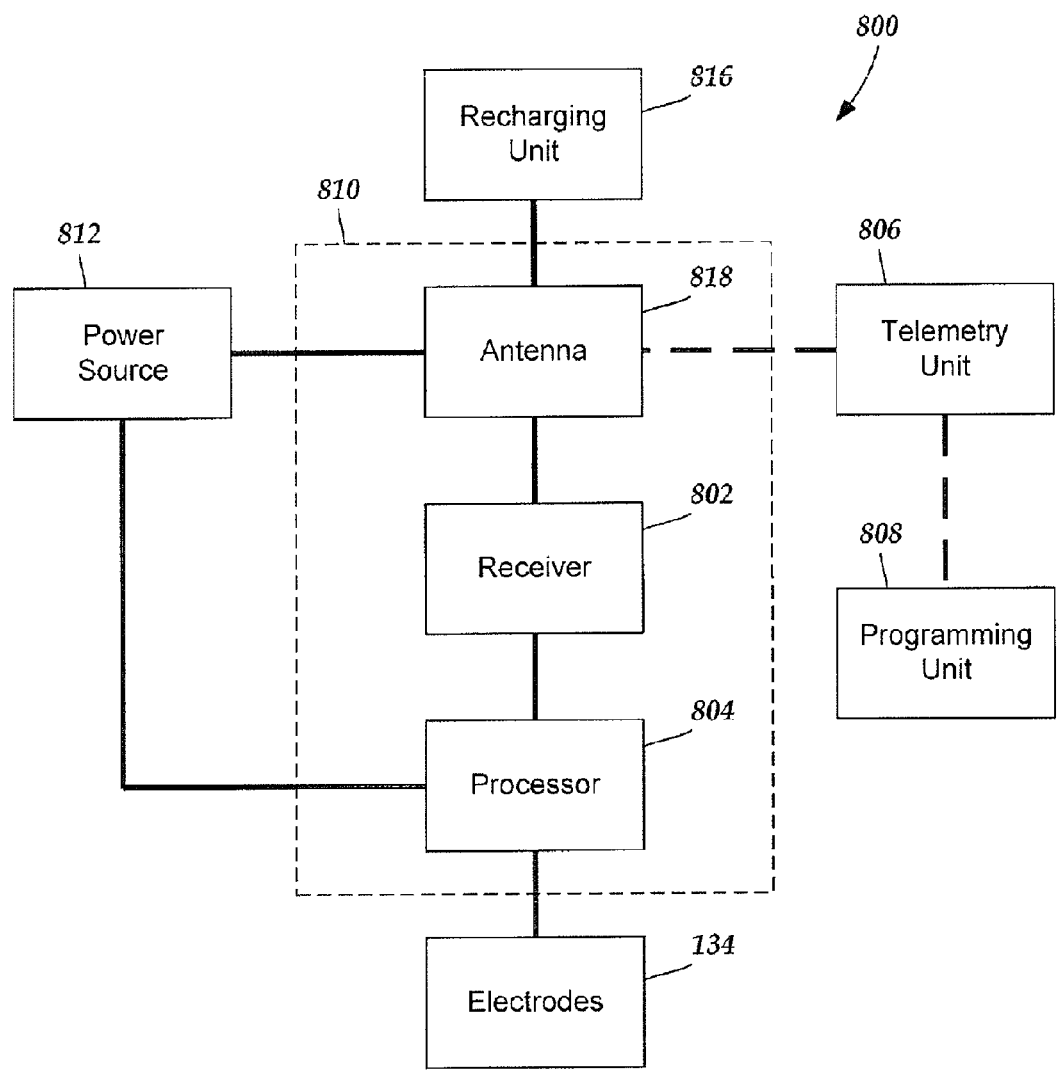
FIG. 8 is a schematic overview of one embodiment of components of a stimulation system, including an electronic subassembly disposed within a control module, according to the invention.

FIG. 8 is a schematic overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in the stimulator references cited herein.

Some of the components (for example, a power source 812, an antenna 818, a receiver 802, and a processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 804 is generally included to control the timing and electrical characteristics of the electrical stimulation system. For example, the processor 804 can, if desired, control one or more of the timing, frequency, strength, duration, and waveform of the pulses. In addition, the processor 804 can select which electrodes can be used to provide stimulation, if desired. In some embodiments, the processor 804 selects which electrode(s) are cathodes and which electrode(s) are anodes. In some embodiments, the processor 804 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802 which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g. RF signals) from an external telemetry unit 806 which is programmed by the programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and the receiver 802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system does not include the antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead having a distal end portion, a proximal end portion, and a longitudinal length, the lead comprising:
    a lead body extending along the lead, the lead body comprising an expandable mesh disposed along the distal end portion of the lead;
    a plurality of electrodes attached to the mesh, each of the electrodes comprising an electrode body and a hook element coupled to the electrode body and hooked into the mesh to hold the electrode in place,
    a plurality of terminals disposed along the proximal end portion of the lead; and
    a plurality of conductors electrically coupling the terminals to the electrodes, wherein a portion of each of the conductors is woven into the mesh,
    wherein each of the plurality of electrodes is attached directly to the mesh and to a one of the plurality of conductors.

2. The electrical stimulation lead of claim 1, further comprising a cylindrical element disposed along at least the distal end portion of the lead, wherein the mesh is contracted around the cylindrical element.

3. The electrical stimulation lead of claim 2, wherein the cylindrical element comprises at least one longitudinal lumen, and wherein a portion of each of the conductors extends within one of the at least one longitudinal lumen.

4. The electrical stimulation lead of claim 1, wherein at least a portion of the mesh is arranged in a form of a paddle at the distal end portion of the lead.

5. The electrical stimulation lead of claim 1, wherein the hook element and the electrode body are formed of a same conductive material.

6. An electrical stimulating system comprising:
    the electrical stimulation lead of claim 1;
    a control module coupleable to the electrical stimulation lead, the control module comprising
        a housing, and
        an electronic subassembly disposed in the housing; and
    a connector for receiving the electrical stimulation lead, the connector having a proximal end, a distal end, and a longitudinal length, the connector comprising
        a connector housing defining a port at the distal end of the connector, the port configured and arranged for receiving the proximal end portion of the electrical stimulation lead, and
        a plurality of connector contacts disposed in the connector housing, the plurality of connector contacts configured and arranged to couple to at least one of the plurality of terminals disposed on the proximal end portion of the electrical stimulation lead.

7. The electrical stimulation lead of claim 1, wherein the mesh is contractible and each electrode of the plurality of electrodes is disposed at a particular longitudinal position along the lead body, wherein the particular longitudinal position of each of the plurality of electrodes along the lead body is changeable by expanding or contracting the mesh.

8. The electrical stimulation lead of claim 1, wherein the electrodes move longitudinally with respect to one another upon expansion or contraction of the mesh.

9. The electrical stimulation lead of claim 1, wherein the lead body consists of the mesh.

10. The electrical stimulation lead of claim 1, wherein each of the electrodes further comprising a linking member attaching the hook element to the electrode body, wherein the linking member has a smaller cross-section than the hook element.

* * * * *